(12) United States Patent
Guan et al.

(10) Patent No.: US 11,497,428 B2
(45) Date of Patent: *Nov. 15, 2022

(54) DEEP INTRACRANIAL ELECTRODE

(71) Applicant: NEUROECHOS MEDICAL (SHENZHEN) CO., LTD, Shenzhen (CN)

(72) Inventors: Xijun Guan, Shenzhen (CN); Xiaolong Mo, Shenzhen (CN)

(73) Assignee: NEUROECHOS MEDICAL (SHENZHEN) CO., LTD, Shenzhen (CN)

( * ) Notice: Subject to any disclaimer, the term of this patent is extended or adjusted under 35 U.S.C. 154(b) by 607 days.

This patent is subject to a terminal disclaimer.

(21) Appl. No.: 16/549,640

(22) Filed: Aug. 23, 2019

(65) Prior Publication Data

US 2021/0015391 A1 Jan. 21, 2021

Related U.S. Application Data

(63) Continuation of application No. PCT/CN2019/096392, filed on Jul. 17, 2019.

(51) Int. Cl.
*A61B 5/291* (2021.01)
*A61B 5/00* (2006.01)
*A61B 5/374* (2021.01)
*A61B 5/055* (2006.01)

(52) U.S. Cl.
CPC ............ *A61B 5/291* (2021.01); *A61B 5/4064* (2013.01); *A61B 5/4094* (2013.01); *A61B 5/6868* (2013.01); *A61B 5/055* (2013.01); *A61B 5/374* (2021.01); *A61B 5/4836* (2013.01)

(58) Field of Classification Search
CPC ......... A61B 5/24; A61B 5/2415; A61B 5/283; A61B 5/287; A61B 5/291; A61B 5/293; A61B 5/6847; A61B 5/6868
See application file for complete search history.

(56) References Cited

U.S. PATENT DOCUMENTS 8,244,346 B2 * 8/2012 Foster ................... A61N 1/056
607/116
8,968,331 B1 * 3/2015 Sochor ............... A61B 17/3468
606/129

(Continued)

FOREIGN PATENT DOCUMENTS

CN 104083823 A * 10/2014
WO WO-2013056243 A1 * 4/2013 ......... A61B 17/3401

*Primary Examiner* — Eun Hwa Kim
(74) *Attorney, Agent, or Firm* — Hamre, Schumann, Mueller & Larson, P.C.

(57) ABSTRACT

A deep intracranial electrode which comprises a flexible wire, an electrode contact, a connector and a shield sleeve, one end of the flexible wire is connected to the electrode contact, the other end connected to the connector; the shield sleeve sheathes around the flexible wire, a sum of a length of a part of the flexible wire arranged outside the shield sleeve and a length of the shield sleeve being adjustable. When the shield sleeve sheaths around the flexible wire, the length of the flexible wire inside the radio-frequency magnetic field of the magnetic resonance equipment may equal to a sum of the length of the shield sleeve and a length of the flexible wire outside the shield sleeve.

15 Claims, 7 Drawing Sheets

(56) References Cited

U.S. PATENT DOCUMENTS

| | | | | |
|---|---|---|---|---|
| 2010/0317921 A1* | 12/2010 | Marple | ................ | A61B 5/6853 600/116 |
| 2012/0253340 A1* | 10/2012 | Stevenson | ............ | H03H 7/0123 607/116 |
| 2018/0116645 A1* | 5/2018 | Nosler | ............... | A61B 10/0283 |

* cited by examiner

DEEP INTRACRANIAL ELECTRODE

CROSS-REFERENCE TO RELATED APPLICATION

This application is a continuation of PCT application No. PCT/CN2019/096392, filed on Jul. 17, 2019. The patent application is hereby incorporated by reference in its entirety.

TECHNICAL FIELD

The present disclosure relates to a medical apparatus and equipment, more particularly, to a deep intracranial electrode.

BACKGROUND

Prior to performing operation to a patient with intractable epilepsy, a deep intracranial electrode is required to monitor intracranial electroencephalograph so as to determine the location of the intractable epilepsy. The deep intracranial electrode normally includes an electrode contact and a connector. The electrode contact is electrically connected to the connector. One end of the deep intracranial electrode arranged with the electrode contact may be implanted surgically into the skull of the patient. The connector may be connected to the electroencephalograph, such that electrophysiological signals collected by the electrode contact may be transmitted to the electroencephalograph.

The electrode contact is connected to the connector via a flexible wire. Since the flexible wire is of a slender structure, it may absorb radio-frequency magnetic field energy generated by a magnetic resonance equipment in the process of magnetic resonance imaging, and produce energy deposition at an end of the flexible wire, which results in heating of the electrode contact connected to the flexible wire. This may damage the patient's brain tissue, or even endanger the patient's life security. Furthermore, the closer the length of the flexible wire is to a resonance length, the more the end of the flexible wire may generate heat. However, the resonance length for a flexible wire varies along with different magnetic resonance equipment, which makes the flexible wire difficult to be compatible with different equipment.

SUMMARY

The present disclosure desires to provide a deep intracranial electrode, and aims to deal with the issue that the electrode contact of the deep intracranial electrode may be heated due to energy deposition of the flexible wire.

In order to deal with the issue above, the present disclosure provides a deep intracranial electrode which comprises a flexible wire, an electrode contact, a connector and a shield sleeve, one end of the flexible wire is connected to the electrode contact, the other end connected to the connector: the shield sleeve sheathes around the flexible wire, a sum of a length of a part of the flexible wire arranged outside the shield sleeve and a length of the shield sleeve being adjustable.

In one embodiment, the length of the shield sleeve is shorter than that of the flexible wire, and the flexible wire is folded inside the shield sleeve.

In one embodiment, the shield sleeve is capable of moving along and relative to the flexible wire so as to change a length of a part of the flexible wire folded inside the shield sleeve.

In one embodiment, the connector comprises a casing and pins arranged inside the casing: a plurality of flexible wires, pins and electrode contacts are arranged, each flexible wire is connected to corresponding pin and corresponding electrode contact.

In one embodiment, the flexible wire and the electrode contact are both made of non-magnetic materials.

In one embodiment, the deep intracranial electrode further comprises a non-elastic sleeve, the non-elastic sleeve sheathing around the flexible wire, and wherein one end of the non-elastic sleeve is capable of being connected to the connector, the other end connected to the fixing nut which is fixed to a skull, and wherein a part of the flexible wire contained inside the non-elastic sleeve is longer than the non-elastic wire.

In one embodiment, the non-elastic sleeve is made of a transparent material.

In one embodiment, one end of the non-elastic sleeve sheathes around the connector, the other end sheathing around the fixing nut.

In one embodiment, the non-elastic sleeve is made of a non-magnetic material.

In one embodiment, the deep intracranial electrode further includes a connecting member, wherein one end of the connecting member connected to the electrode contact, the other end connected to the connector; and a part of the connector between the electrode contact and the connector is shorter than a part of the flexible wire between the electrode contact and the connector.

In one embodiment, the connector is made of a tensile material.

In one embodiment, the deep intracranial electrode further includes a flexible insulating sleeve sheathing around the flexible wire, one end of the flexible insulating sleeve connected to the electrode contact, the other end connected to the connector; the deep intracranial electrode further includes a rigid support rod, the rigid support rod passing through the flexible insulating sleeve and located at one end of the flexible insulating sleeve connected to the electrode contact.

In one embodiment, the rigid support rod is made of a shape memory material.

In one embodiment, the deep intracranial electrode further includes an end electrode, the end electrode connected to the rigid support rod and electrically connected to the connector via the flexible wire.

In one embodiment, the electrode contacts are of an annular shape.

In the deep intracranial electrode above, by arranging the shield sleeve, it may shield radio-frequency electromagnetic wave generated by magnetic resonance equipment. When the shield sleeve sheaths around the flexible wire, the length of the flexible wire inside the radio-frequency magnetic field of the magnetic resonance equipment may equal to a sum of the length of the shield sleeve and a length of the flexible wire outside the shield sleeve. Therefore, the user may change the length of the shield sleeve and/or the length of the flexible wire outside the shield sleeve as necessary such that the sum of the length of the shield sleeve and the length of the flexible wire arranged outside the shield sleeve is deviated from the resonance length of the flexible wire, reducing heating risk for the end of the flexible wire.

BRIEF DESCRIPTION OF THE ACCOMPANYING DRAWINGS

In order to describe the embodiments of the present disclosure and the prior art more clearly, the drawings required for describing the embodiments of the present disclosure and the prior art are briefly introduced. Apparently, the drawings below merely represent some embodiments of the present application. For those ordinarily skilled in the field, alternative drawings may be obtained without pay creative works.

Figure 1:
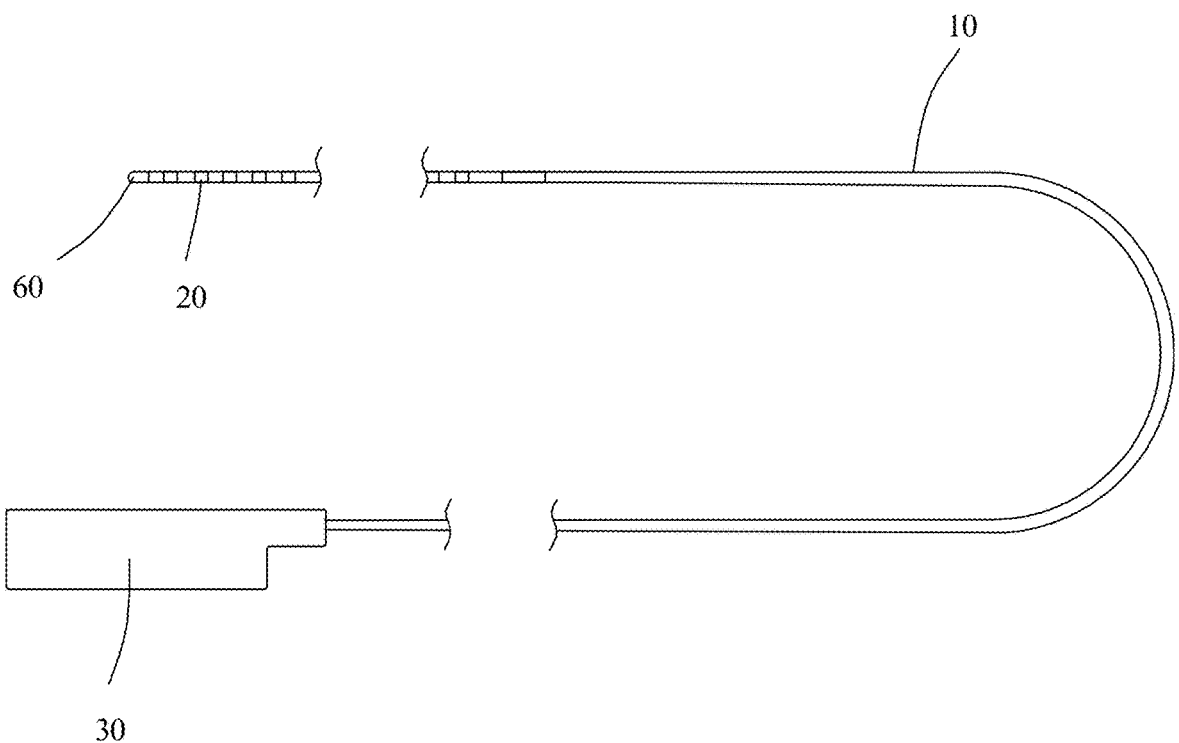
FIG. 1 is a schematic view of a partial structure of a deep intracranial electrode according to an embodiment of the present application.

Reference numbers in the description are as follows:
100. deep intracranial electrode:
10. flexible wire:
20 electrode contact;
30. connector;
40. shield sleeve:
50 rigid support rod:
60. end electrode;
70. non-elastic sleeve:
80 flexible insulating sleeve:
200. fixing nut.

DETAILED DESCRIPTION OF ILLUSTRATED EMBODIMENTS

Technical solutions in the embodiments of the present disclosure will be described below clearly and completely with reference to the drawings. Obviously, the embodiments described herein are only some, but no exclusive embodiments of the present disclosure Based on the embodiments described in this present disclosure, all other embodiments obtained by those ordinarily skilled in the field without paying creative works should fall within the scope of the present application.

One embodiment of the present application provides a deep intracranial electrode 100 to detect electrophysiological activities in deep brain tissue of a patient. The deep intracranial electrode 100 comprises a flexible wire 10, an electrode contact 20 and a connector 30. One end of the flexible wire 10 is connected to the electrode contact 20, the other end connected to the connector 30.

In the embodiment, the connector 30 comprises a casing and pins arranged inside the casing. A plurality of flexible wires 10, pins and electrode contacts 20 are provided. Each flexible wire 10 is connected to corresponding pin and corresponding electrode contact 20. Each of the pins inside the connector 30 is independent from each other with high integration level, which is convenient for connection to an electroencephalograph.

Figure 2:
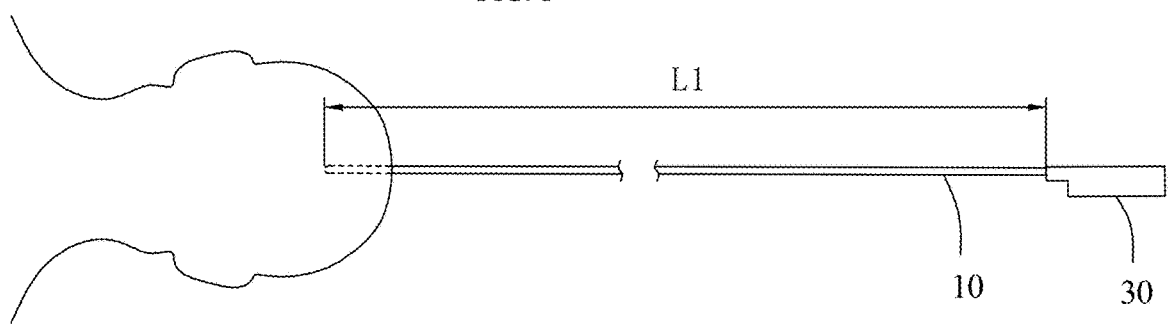
FIG. 2 is a schematic view of an original state of a flexible wire when the deep intracranial electrode in FIG. 1 is implanted into the skull of a patient.
Figure 3:
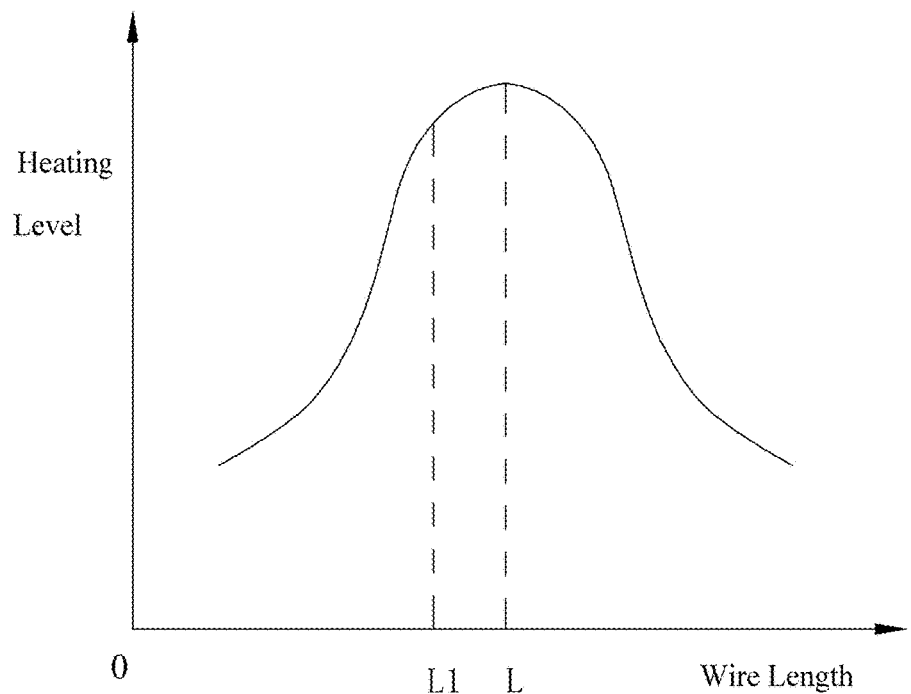
FIG. 3 is a relation graph of a heating level of the flexible wire of the deep intracranial electrode in FIG. 2 versus a length of the flexible wire.

As shown in FIG. 2, one end of the deep intracranial electrode 100 arranged with the electrode contact 20 is capable of being implanted into the skull of the patient, such that the electrode contact 20 may collect electrophysiological signals in deep brain tissue of the patient. Since the flexible wire 10 is of a slender structure, it may absorb radio-frequency magnetic field energy generated by a magnetic resonance equipment, and produce energy deposition at an end of the flexible wire 10, which results in heating of the electrode contact 20 connected to the flexible wire 10. As shown in FIG. 3, the heating level of the flexible wire 10 of the deep intracranial electrode 100 varies along with the length of the flexible wire 10 with a peak value. The length of the flexible wire 10 corresponding to the peak value is a resonance length of the flexible wire 10. For illustrative purpose, the resonance length of the flexible wire 10 is called L. As shown in FIG. 3, the further away the length of the flexible wire 10 is from the resonance length L of the flexible wire 10, the lower the heating level of the flexible wire 10 is.

Figure 4:
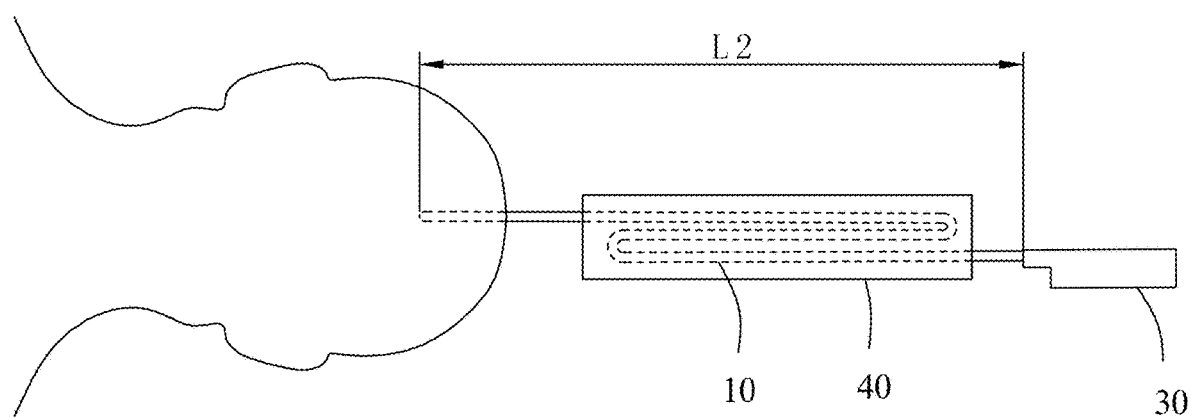
FIG. 4 is a schematic view of the deep intracranial electrode in FIG. 2 with the length of the flexible wire adjusted.
Figure 5:
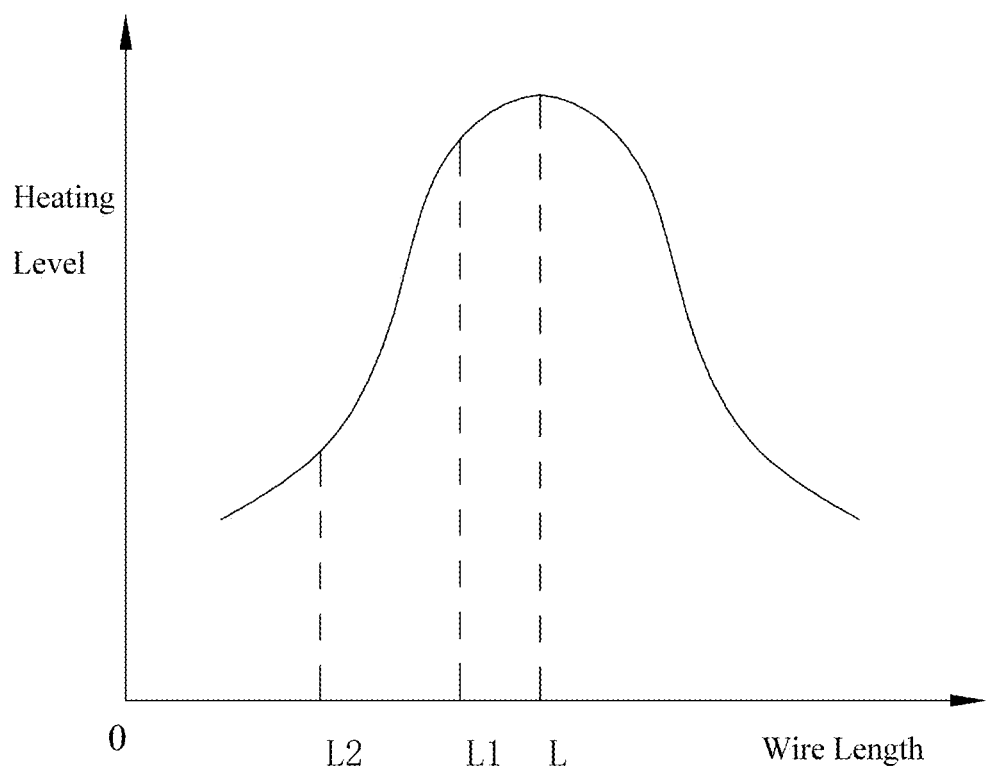
FIG. 5 is a relation graph of a heating level of the flexible wire of the deep intracranial electrode in FIG. 4 versus a length of the flexible wire.

Ai shown in FIG. 4, in order to lower heating level of the flexible wire 10. The deep intracranial electrode 100 in the present embodiment further includes a shield sleeve 40. The shield sleeve 40 may sheath around the flexible wire 10 so as to shield the electromagnetic wave of the magnetic resonance radio-frequency magnetic field By adopting proper materials, the shield sleeve 40 may also effectively shield electromagnetic wave in a frequency band (30 MHZ-300 HHZ) of the magnetic resonance radio-frequency magnetic field. The shield sleeve 40 is shorter than the flexible wire 10. Partial structure of the flexible wire 10 is folded inside the shield sleeve 40. By arranging the shield sleeve 40 which may shield radio-frequency electromagnetic wave generated by a magnetic resonance equipment, the length of the flexible wire 10 inside the radio-frequency magnetic field of the magnetic resonance equipment may equal to a sum of the length of the shield sleeve 40 and a length of the flexible wire 10 outside the shield sleeve 40. For illustrative purpose, the actual length of the flexible wire 10 is called L1, the equivalent length of the flexible wire 10 is called L2. As shown in FIG. 5, the equivalent length L2 of the flexible wire 10 is lower than the actual length L1 of the flexible wire 10, and 12 is further away from the resonance length that L1 is. Therefore, the heating level of the end of the flexible wire 10 is reduced, improving safety performance of the deep intracranial electrode 100. In order to avoid the shield sleeve 40, which sheaths around the flexible wire 10, from moving relative to the flexible wire 10, the shield sleeve 40 may be fasten to the flexible wire 10 with a ribbon or a hoop. Surely, the shield sleeve 40 may be avoided from move randomly by controlling an inner diameter of the shield sleeve 40.

It is to be understood that the shield sleeve 40 may adopt a braided network pipe, metal coated hose or the like, which is convenient for the shield sleeve 40 to sheath around the flexible wire 10, furthermore, the flexible wire 10 may still keep flexible after sheathed by the shield sleeve 40, which is convenient for use.

Figure 6:
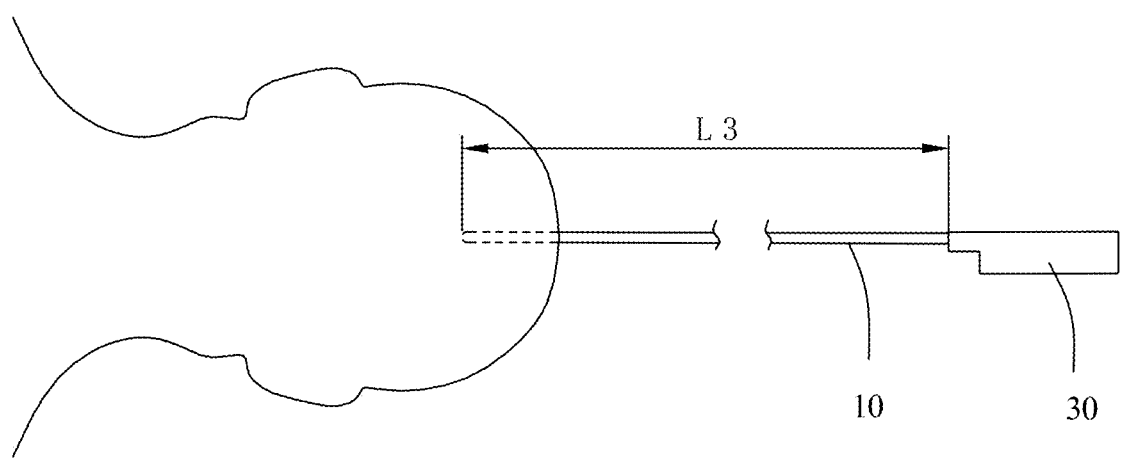
FIG. 6 is a schematic view of an original state of a flexible wire when a deep intracranial electrode with another length is implanted into the skull of the patient.
Figure 7:
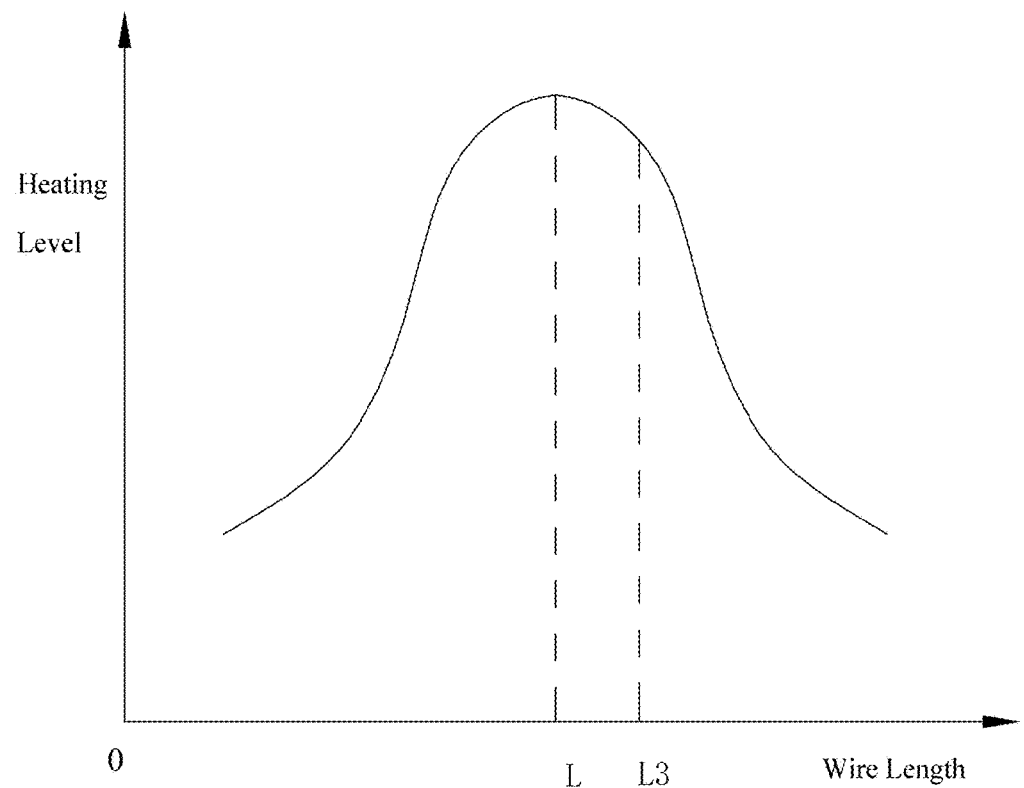
FIG. 7 is a relation graph of a heating level of the flexible wire of the deep intracranial electrode in FIG. 6 versus a length of the flexible wire.
Figure 8:
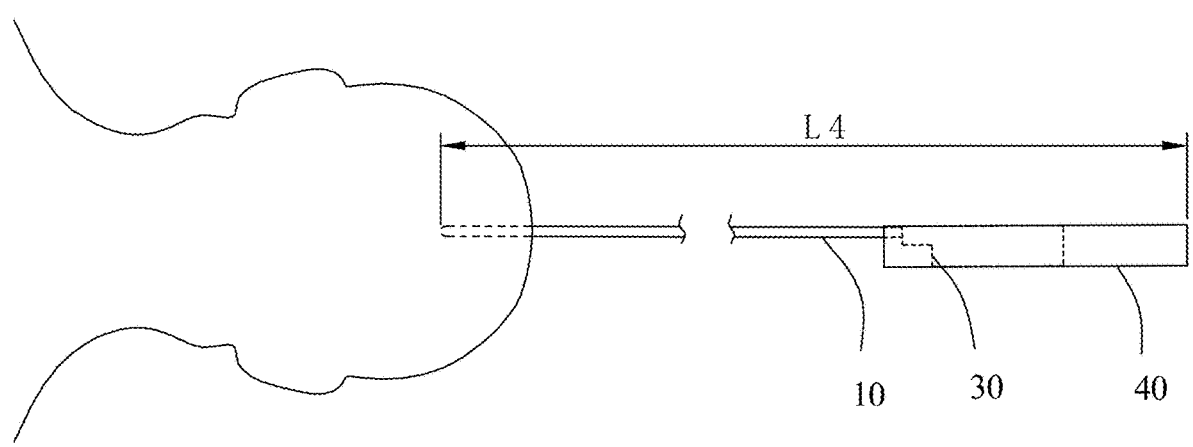
FIG. 8 is another schematic view of the deep intracranial electrode in FIG. 6 with the length of the flexible wire adjusted.
Figure 9:
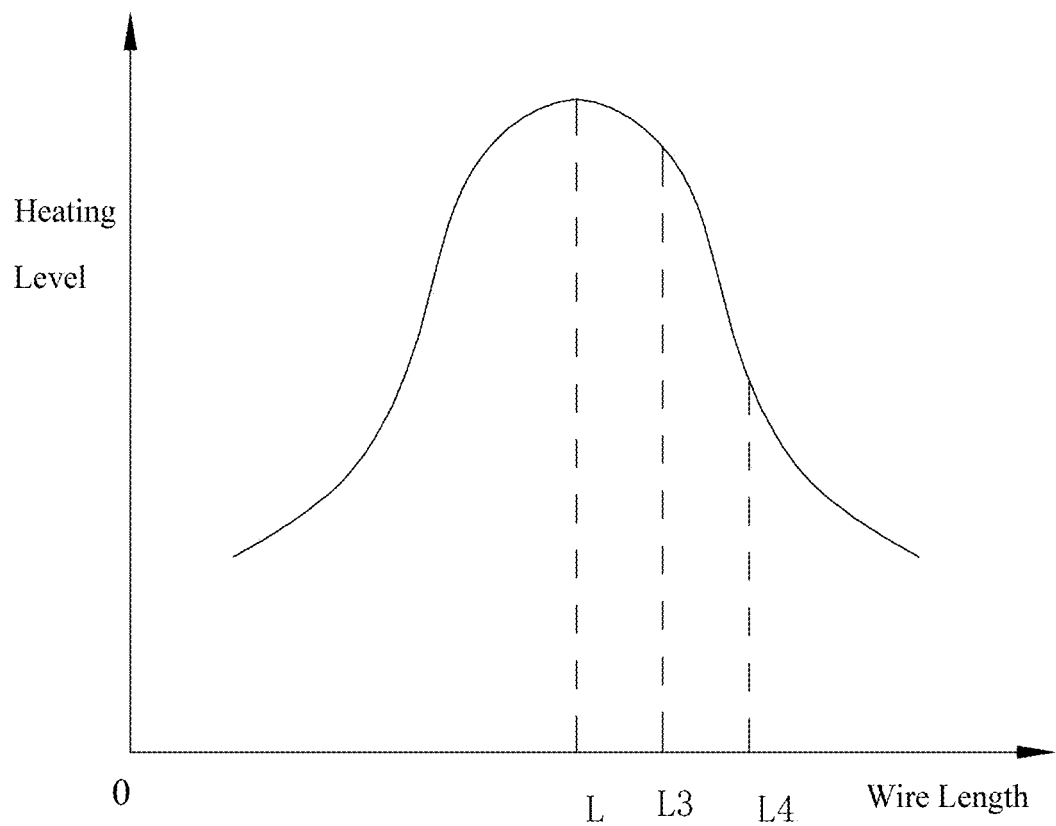
FIG. 9 is a relation graph of a heating level of the flexible wire of the deep intracranial electrode in FIG. 8 versus a length of the flexible wire.

As shown in FIG. 6 and FIG. 7, in another embodiment the actual length of the flexible wire 10 is greater than the resonance length L of the flexible wire 10. In order to lower heating level of the flexible wire 10, the shield sleeve 40 sheaths around the flexible wire 10, such that the equivalent length of the flexible wire 10 is greater than the actual length L of the flexible wire 10. For illustrative purpose, the actual length of the flexible wire 10 is called 13, the equivalent length of the flexible wire 10 is called L4. As shown in FIG. 8, the shield sleeve 40 may move axially along and relative to the flexible wire 10 so as to change the length of a part of the shield sleeve 40 sheathing around the flexible wire 10. As shown in FIG. 9, the equivalent length L4 of the flexible wire 10 is greater than the actual length L3 of the flexible wire 10, and L4 is further away from the resonance length that L3 is. Therefore, the heating of the end of the flexible wire 10 is reduced, improving safety performance of the deep intracranial electrode 100.

It is to be understood that the resonance length L of the flexible wire 10 is relevant to parameters of the magnetic resonance equipment. For an identical flexible wire 10, resonance length L varies with different magnetic resonance equipment. The length of the part of the flexible wire 10 located inside the shield sleeve 40 may be varied according to user's actual need, such that the equivalent length of the flexible wire 10 is further away from the resonance length L of the flexible wire 10 than the actual length of the flexible wire 10 is, lowering beating risk of the end of the flexible wire 10. Furthermore, the user may choose shield sleeves 40 with different lengths, so as to change the sum of the length of the shield sleeve 40 and a length of the flexible wire 10 arranged outside the shield sleeve 40.

It's worth mentioning that in the present embodiment, the flexible wires 10, the electrode contacts 20 and the pins are all made of non-magnetic materials, such as non-magnetic metal materials, conductive polymer materials, carbon nanotubes or graphene materials. The non-magnetic materials may avoid the flexible wires 10, the electrode contacts 20 and the pins from interfering magnetic field environment of the magnetic resonance equipment, so as to avoid the magnetic resonance equipment from generating artifacts.

Figure 10:
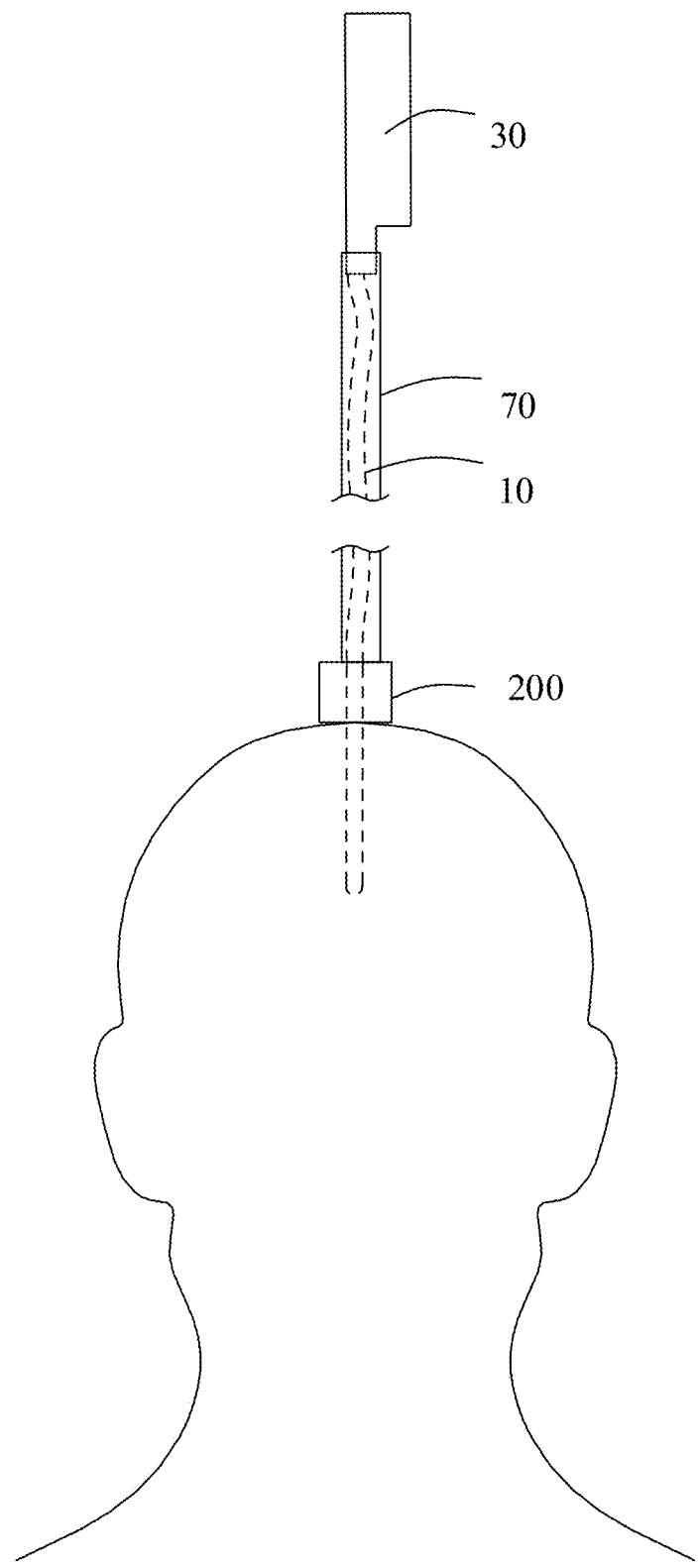
FIG. 10 is a schematic view of the deep intracranial electrode in FIG. 1 implanted into the skull of the patient.

Furthermore, in the present embodiment, as shown in FIG. 10, the deep intracranial electrode 100 further includes a non-elastic sleeve 70 which may sheath around the flexible wire 10. One end of the non-elastic sleeve 70 is connected to the connector 30, the other end connected to the fixing nut 200 that is fixed to the skull. Therefore, when the deep intracranial electrode 100 is under a pulling force, the fixing nut 200 may avoid the non-elastic sleeve 70 from moving, thereby avoiding the deep intracranial electrode 100 from being pulled out.

Furthermore, a part of the flexible wire 10 contained within the non-elastic sleeve 70 is longer than the non-elastic sleeve 70. While the deep intracranial electrode 100 is under a pulling force, the non-elastic sleeve 70 bears the tension, and the flexible wire 10 inside the non-elastic sleeve 70 may still keep a loose state all the time and avoid being damaged by the tension.

Furthermore, the non-elastic sleeve 70 is made of a transparent material, which is convenient for a user to check the status of the flexible wire 10 contained inside the non-elastic sleeve 70. Furthermore, the non-elastic sleeve 70 may also adopt a non-magnetic material, thereby avoiding interference of radio-frequency electromagnetic wave in the process of transmitting electrophysiological signals.

Furthermore, one end of the non-elastic sleeve 70 sheathes around the connector 30, the other end sheathing around the fixing nut 200. In addition, the non-elastic sleeve 70 may fasten to the connector 30 and the fixing nut 200 via a hoop. Therefore, the non-elastic sleeve 70 is merely connected to the connector 30 and the fixing nut 200 when necessary, and may be replaced if damaged.

It's worth mentioning that the deep intracranial electrode 100 in the present embodiment further includes a connecting member (not shown), one end of the connecting member connected to the electrode contact 20, the other end connected to the connector 30. Furthermore, a part of the connecting member between the electrode contact 20 and the connector 30 is shorter than a part of the flexible wire 10 between the electrode contact 20 and the connector 30. When the deep intracranial electrode 100 is under a pulling force, since the part of the connecting member between the electrode contact 20 and the connector 30 is shorter than the part of the flexible wire 10 between the electrode contact 20 and the connector 30, the connecting member may bear the tension, improving tensile strength of the deep intracranial electrode 100 and avoiding the deep intracranial electrode 100 from broken accidentally in the process of detection. In the present embodiment, the material of the connecting member is a tensile material such as fiberglass, which is easy to obtain and will not interfere radio-frequency magnetic field of the magnetic resonance equipment. Surely, in alternative embodiments, the connecting member may adopt alternative materials with greater tensile strength.

Furthermore, the deep intracranial electrode 100 further includes a flexible insulating sleeve 80 sheathing around the flexible wire 10, one end of the flexible insulating sleeve 80 connected to the electrode contacts 20, the other end connected to the casing. It is to be understood that the flexible insulation tube 80 integrates multiple flexible wires into a bundle, thus making the flexible wires 10 arranged more orderly. It may also avoid the flexible wires 10 from exposure, improve the safety performance and service life of the deep intracranial electrode 100, and better the data transmission stability. In addition, the electrode contacts 20 in the present embodiment are of an annular structure. The electrode contacts 20 sheath around the flexible insulating tube 80, which increases contact area between the electrode contacts 20 and the patient's deep brain tissue.

Figure 11:
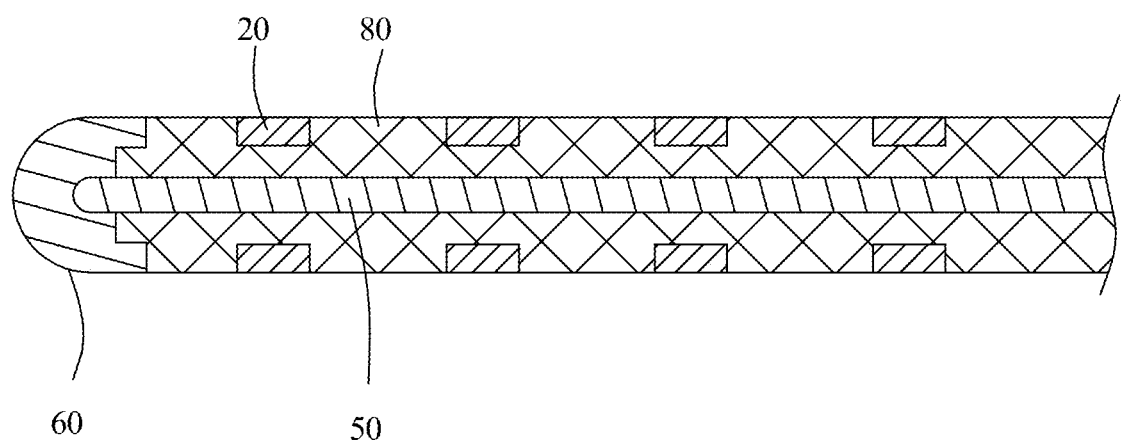
FIG. 11 is a schematic view of a partial structure of the deep intracranial electrode in FIG. 1.

As shown in FIG. 11, the deep intracranial electrode 100 further includes a rigid support rod with a certain stiffness. The rigid support rod 50 passes through the flexible insulating sleeve 80, such that the flexible insulating sleeve 80 is straight, therefore, one end of the deep intracranial electrode 100 connected to the electrode contact 3 may be implanted into the skull the patient conveniently. Furthermore, the rigid support rod 50 in the present embodiment is made of a shape memory material, such as a shape memory alloy material, or a shape memory ceramic material. Therefore, the rigid support rod 50 may recover to its original shape after being bent under external forces, avoiding scraping the deep intracranial electrode 100 completely for the bending of the rigid support rod 50.

Furthermore, the deep intracranial electrode 100 further includes an end electrode 60. The end electrode 60 is connected to the rigid support rod 50 and electrically connected to the connector 30 via the flexible wire 10. The end electrode 60 may collect electrophysiological signals of a patient's deep brain tissue. Furthermore, the end electrode 60 also provides therein with an electromagnetic induction element for marking the location of the end electrode 60, such that location information of the end electrode 60 may be fed back to external equipment.

Disclosures above only describe preferable embodiments of the present application, and should not be deemed as limiting the protection scope of the present application Equivalent modifications based on the appended claims should also fall within the protection scope of the present application.

What is claimed is:

1. A deep intracranial electrode adapted to be used with a magnetic resonance equipment, comprising:
   one or more flexible wires, wherein an entire longitudinal length of the one or more flexible wires defines an actual length having a heating value when the one or more flexible wires absorbs a radio-frequency magnetic field wave generated by the magnetic resonance equipment;
   one or more electrode contacts connected to one end of the one or more flexible wire;
   a connector connected to another end of the one or more flexible wires;
   a shield sleeve sheathes around the one or more flexible wires and configured to shield from the radio-frequency magnetic field generated by the magnetic resonance equipment and lower the heating value of the one or more flexible wire; and
   wherein an equivalent length of the one or more flexible wires inside the radio-frequency magnetic field generated by the magnetic resonant equipment equals to a sum of the length of the shield sleeve and a length of the one or more flexible wires outside the shield sleeve, and wherein the equivalent length is different from the actual length of the one or more flexible wires such that a heating value corresponding to the equivalent length is lower than the corresponding heating value of the actual length of the one or more flexible wires when the one or more flexible wires absorbs the radio-frequency magnetic field wave during a magnetic resonance imaging.

2. The deep intracranial electrode of claim 1, wherein the length of the shield sleeve is shorter than that of the one or more flexible wires, and the one or more flexible wires can be folded inside the shield sleeve.

3. The deep intracranial electrode of claim 1, wherein the shield sleeve can be moved along and relative to the one or more flexible wires while the deep intracranial electrode is in a detecting status, so as to change a length of a part of the one or more flexible wires folded inside the shield sleeve.

4. The deep intracranial electrode of claim 1, wherein the connector comprises a casing and a plurality of pins arranged inside the casing, and each of the one or more flexible wires is connected with a corresponding one of the plurality of pins and a corresponding one of the one or more electrode contacts.

5. The deep intracranial electrode of claim 1, wherein the one or more flexible wires and the one or more electrode contacts are both made of non-magnetic materials.

6. The deep intracranial electrode of claim 1, further comprising a non-elastic sleeve, the non-elastic sleeve sheathing around the one or more flexible wires, and wherein one end of the non-elastic sleeve is connected to the connector, the other end is connected to a fixing nut which is fixed to a skull, and wherein the one or more flexible wires contained inside the non-elastic sleeve is longer than the non-elastic sleeve.

7. The deep intracranial electrode of claim 6, wherein the non-elastic sleeve is made of a transparent material.

8. The deep intracranial electrode of claim 6, wherein one end of the non-elastic sleeve sheathes around the connector, the other end sheathing around the fixing nut.

9. The deep intracranial electrode of claim 6, wherein the non-elastic sleeve is made of a non-magnetic material.

10. The deep intracranial electrode of claim 1, wherein the deep intracranial electrode further includes a connecting member, one end of the connecting member connected to the one or more electrode contacts, the other end connected to the connector, and a part of the connecting member between the one or more electrode contacts and the connector is shorter than a part of the one or more flexible wires between the one or more electrode contacts and the connector.

11. The deep intracranial electrode of claim 10, wherein the connector is made of a tensile material.

12. The deep intracranial electrode of claim 1, wherein the deep intracranial electrode further includes a flexible insulating sleeve sheathing around the one or more flexible wires, one end of the flexible insulating sleeve connected to the one or more electrode contacts, the other end connected to the connector; the deep intracranial electrode further includes a rigid support rod, the rigid support rod passing through the flexible insulating sleeve and located at one end of the flexible insulating sleeve with the one or more electrode contacts.

13. The deep intracranial electrode of claim 12, wherein the rigid support rod is made of a shape memory material.

14. The deep intracranial electrode of claim 12, wherein the deep intracranial electrode further includes an end electrode, the end electrode connected to the rigid support rod and an endpoint of the one end of the one or more flexible wires, and electrically connected to the connector via each one of the one or more flexible wires.

15. The deep intracranial electrode of claim 1, wherein the one or more electrode contacts are of an annular shape.

* * * * *